(12) United States Patent
Lawrence et al.

(10) Patent No.: US 9,504,740 B2
(45) Date of Patent: *Nov. 29, 2016

(54) HAEMOPHILUS PARASUIS VACCINE SEROVAR TYPE FOUR

(71) Applicant: MERIAL LIMITED, Duluth, GA (US)

(72) Inventors: Paulraj Kirubakaran Lawrence, Worthington, MN (US); Russell F. Bey, Arden Hills, MN (US)

(73) Assignee: MERIAL, INC., Duluth, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/507,397

(22) Filed: Oct. 6, 2014

(65) Prior Publication Data

US 2015/0098968 A1 Apr. 9, 2015

Related U.S. Application Data

(60) Provisional application No. 61/886,991, filed on Oct. 4, 2013.

(51) Int. Cl.
*A61K 39/102* (2006.01)
*A61K 39/00* (2006.01)

(52) U.S. Cl.
CPC ....... *A61K 39/102* (2013.01); *A61K 2039/521* (2013.01); *A61K 2039/552* (2013.01); *A61K 2039/70* (2013.01)

(58) Field of Classification Search
None
See application file for complete search history.

(56) References Cited

U.S. PATENT DOCUMENTS 8,404,253 B2 * 3/2013 Oliveira ............... A61K 39/102
424/256.1
2010/0255035 A1 * 10/2010 Oliveira ............... A61K 39/102
424/256.1

FOREIGN PATENT DOCUMENTS

CN 101721696 * 6/2010
WO WO 2011/131789 A1 10/2011

OTHER PUBLICATIONS

ParaSail vaccine brochure obtained from www on Nov. 24, 2015.*
Tadjine et al (Microbiology, 150:3935-45, 2004).*
English translation of CN 101721696.*
Database WPI Week 201381 Thomson Scientific AN 2013-T25429 XP002734902 & CN 103 194 413 A (Jiangsu Agric Sci Inst) Jul. 10, 2013 abstract.
Database WPI Week 201337 Thomson Scientific AN 2013-H24025 XP002734903 & CN 102 908 615 A (Pulike Bioengineering Co Ltd) Feb. 6, 2013 abstract.
Database WPI Week 201226 Thomson Scientific AN 2012-B99507 XP002734904 & CN 102 329 746 A (Wuhan Keqian Animal Biological Prod Co) Jan. 25, 2012 abstract.
Database WPI Week 201256 Thomson Scientific AN 2012-J40909 XP002734905 & CN 102 499 982 A (Qingdao Yebio Bioengineering Co Ltd) Jun. 20, 2012 abstract.
"Summary of Product Characteristics" Nov. 2012 XP002734906 http://mri.medagencies.org/download/UK_V_0279_001_FinalSPC.pdf.
PK Lawrence et al., "Genome Wide Association Studies of Virulent and Avirulent *Haemophilus parasuis* Serotype 4 Strains" Genome Announcements vol. 2(5) Sep. 4, 2014 pp. 1-2 XP055163227 DOI: 10.1128/genomeA.00884-14.
English translation of CN 103 194 413 A abstract.
English translation of CN 102 908 615 abstract.
English translation of CN 102 329 746 A abstract.
English translation of CN 102 499 982 A abstract.

* cited by examiner

*Primary Examiner* — Patricia Duffy
(74) *Attorney, Agent, or Firm* — Judy Jarecki-Black; Ruoying Chen; Merial Inc.

(57) ABSTRACT

The present invention is a *Haemophilus parasuis* vaccine against serovar type 4 capable of triggering a protective immune response when administered to pigs as a killed vaccine. The present invention is also a method for vaccinating swine against *Haemophilus parasuis* infection, serovar type 4, by a) clonally propagating one or more cells which are capable of triggering an immune response against *Haemophilus parasuis* infection, serovar type 4, that protects the pig against *Haemophilus parasuis* infection, and b) combining an immunologically effective amount of the cells with a veterinarily acceptable carrier in a form suitable for administration as a vaccine to the pig, and c) administering as a killed vaccine. The cell culture is from a pathogenic parent strain.

8 Claims, 1 Drawing Sheet

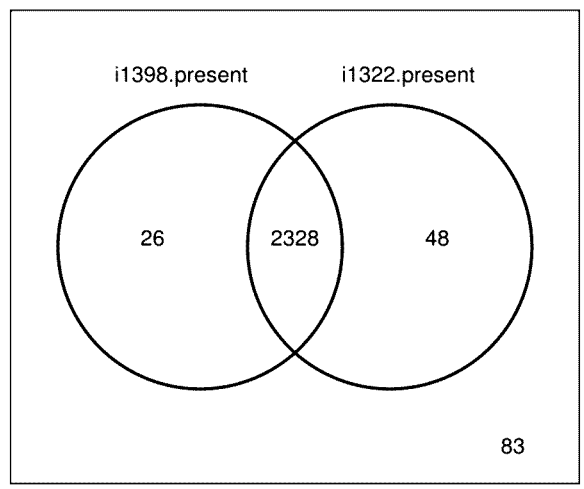

HAEMOPHILUS PARASUIS VACCINE SEROVAR TYPE FOUR

STATEMENT REGARDING SEQUENCE LISTING

The Sequence Listing associated with this application is provided in text format in lieu of a paper copy, and is hereby incorporated by reference into the specification. The name of the text file containing the Sequence Listing is H parasuis genomic—Paul Lawrence_ST25. The text file is 8,732 KB; it was created on 2 Oct. 2013; and it is being submitted electronically via EFS-Web, concurrent with the filing of the specification.

BACKGROUND OF THE INVENTION

*Haemophilus parasuis* is a γ-proteobacteria and is classified in the Pasteurellaceae family. *H. parasuis* is a rod-shaped, non-haemolytic, gram-negative nicotinamide adenine dinucleotide (NAD)-dependent bacterium (Biberstenia and White, 1969; Nicolet 1992). *H. parasuis* is a commensal of the upper respiratory tract of healthy pigs. It is also an important pathogen and the etiological agent of Glasser's disease, which is typically characterized by fibrinous polyserositis, polyarthritis, meningitis and sometimes acute pneumonia and septicemia (Amano et al., 1994; Peet et al., 1983; Little, 1970). This disease is one of the main causes of swine mortality in the US and swine industries worldwide, resulting in huge economic losses.

Recent studies have demonstrated that non-virulent strains are more prevalent in the upper respiratory tract than virulent strains however, they are not protected against systemic infection by virulent strains.

Based on heat-stable antigens and gel diffusion test data, fifteen serovars of *H. parasuis* have been identified so far, but a high percentage of the field isolates are non-typable (Kielstein and Rapp-Gabrielson, 1992). Different serovars of *H. parsuis* exhibit different virulence, ranging from highly virulent to nonvirulent. Of the 15 recognized serovars, serovar 5 strains are isolated more frequently worldwide than any other. The serovar 5 strain is also frequently isolated from respiratory and systemic infection in pigs and is highly virulent (Rapp-Gabrielson and Gabrielson, 1992; Blackall et al., 1996; Oliveira, 2003). Furthermore, it has emerged recently as one of the major causes of neonatal mortality in the pig industry worldwide as well.

Newport Laboratories developed a commercial vaccine (ParaSail) against *H. parasuis* infection using a highly virulent serovar 5 North American field isolate. This vaccine—when used as recommended by swine producers—is highly effective in mitigating *H. parasuis* infection in the United States. Recently, however, a few farms in the Midwestern United States using this vaccine had reported outbreaks of severe pneumonia. Tissue samples obtained by Newport Laboratories during the 2011-2012 outbreak yielded a highly virulent isolate of *H. parasuis* serotype 4 strains. The reason for outbreak was unknown at the time, although internal challenge studies showed that ParaSail vaccine when used at $10^9$ CFU per dose protects pigs against *H. parasuis* serotype 4 strains.

Like the rest of the members of Pasteurellaceae, *H. parasuis* has a large number of virulence and virulence-associated genes. These include lipopolysaccharide (LPS), capsular polysaccharide, adhesins/fimbriae, outer membrane proteins, neuraminidase, iron and heavy metal acquisition and transport systems (Amano et al., 1994; Biberstein, 1990; Munch et al., 1992; Zucker et al., 1996; Morozumi and Nicolet, 1986). The molecular basis underlying these candidate virulence factors is yet to be fully elucidated, however, due to the complex gene regulatory mechanisms involved. *H. parasuis* strains exhibit high heterogeneity at the molecular level, mostly due to recombination or lateral gene transfer. In order to elucidate the possible reasons behind the 2011-2012 Midwest outbreaks at the molecular level we sequenced the genomes of two *H. parasuis* serotype 4 isolates and performed a 3-way comparative genomic analysis against our Parasail vaccine strain (used as a reference; SEQ ID NO. 1). The two *H. parasuis* serotype 4 isolates were obtained from Newport Laboratories case numbers 12-1322 (SEQ ID NO. 2; GenBank accession number JJNQ00000000; ST4-1) and 11-1398-2 (SEQ ID NO. 3; GenBank accession number JJNR00000000; ST4-2).

Although neither the mechanisms involved in the protective immunity following controlled exposure nor the identity of antigens which provide protective immunity are clear at this time, it is known that protective immunity can be induced by such exposure.

The pork industry is in immediate need of a safe and efficacious product capable of aiding the prevention of disease, specifically *Haemophilus parasuis* serotype 4.

SUMMARY OF THE INVENTION

In one aspect, the invention is a vaccine for *Haemophilus parasuis*, serovar type 4, comprising a veterinarily acceptable carrier and an immunologically effective amount of killed bacterin or bacterial cell culture capable of triggering an immune response that protects the pig against *Haemophilus parasuis* infection. In another aspect, the invention is a vaccine wherein the DNA sequence of the bacterin or bacterial cell culture includes SEQ ID NO: 2. In another aspect, the invention is a vaccine wherein the DNA sequence of the bacterin or bacterial cell culture includes SEQ ID NO. 3. In another aspect, the vaccine of the invention includes the ParaSail vaccine against *Haemophilus parasuis*, serovar type 5.

In another embodiment, the invention is a method for vaccinating swine against *Haemophilus parasuis* infection, serovar type 4, comprising the steps of a) clonally propagating one or more cells which are capable of triggering an immune response against *Haemophilus parasuis* infection, serovar type 4, that protects the pig against *Haemophilus parasuis* infection, and b) combining an immunologically effective amount of the cells with a veterinarily acceptable carrier in a form suitable for administration as a vaccine to the pig, and c) administering as a killed vaccine. In one aspect, the method for vaccinating swine with a killed vaccine includes the DNA sequence of SEQ ID NO. 2. In another aspect, the method for vaccinating swine with a killed vaccine includes the DNA sequence of SEQ ID NO. 3. In yet another aspect, the method for vaccinating swine includes administration of the Parasail vaccine against *Haemophilus parasuis*, serovar type 5.

BRIEF DESCRIPTION OF FIGURES

FIG. 1: Venn diagram representing the number of genes unique to *H. parasuis* ST4 isolates 12-1322 (i.e., ST4-1; SEQ ID NO. 2) and 11-1398-2 (i.e., ST4-2; SEQ ID NO. 3) compared with the ParaSail vaccine (SEQ ID NO. 1).

DETAILED DESCRIPTION OF THE INVENTION

Applicants have discovered that the commercially available Parasail vaccine against *Haemophilus parasuis* (serovar type 5) may not sufficiently vaccinate swine against a mutant strain of *Haemophilus parasuis* serovar type 4 (i.e., ST4). A killed vaccine is herein presented capable of triggering an immune response that protects pigs against *Haemophilus parasuis* ST4 infection.

The present invention further provides a method for preparing a vaccine to protect pigs against *Haemophilus parasuis* infection, serovar type 4, comprising selecting and clonally propagating one or more cells which are capable of triggering an immune response against *Haemophilus parasuis* infection, serovar type 4, that protects the pig against *Haemophilus parasuis* infection when administered as a killed vaccine, and combining an immunologically effective amount of the cells with a veterinarily acceptable carrier in a form suitable for administration as a live vaccine to the pig.

Example 1

The objective of this study was to determine if pigs vaccinated with ParaSail alone or in combination with an autogenous bacterin were protected against disease associated with *Haemophilus parasuis* (*H. parasuis*) type 4 (11-1398-2; SEQ ID NO. 3). This study included three groups; Group A (n=15) received 1 mL ParaSail per label directions and 1 mL of an autogenous type 4 bacterin, Group B (n=15) received 1 mL ParaSail per label directions, followed by 1 mL of an autogenous type 4 bacterin two weeks later and Group C (n=14) received 1 mL of ParaSail (adjuvanted with Quil and Trigen) per label directions. The last group (D) (n=13) served as non-vaccinated controls. All enrolled pigs were challenged with an *H. parasuis* type 4 (11-1398-2; SEQ ID NO. 3) field strain 40 days following initial vaccination. Challenged animals were observed daily for clinical signs of disease and death. Five days following challenge, all surviving animals were sacrificed and necropsied. Animals with lesions typical of *H. parasuis* were recorded.

ParaSail, when paired with the autogenous type 4, protected better than when ParaSail was given alone. Furthermore, Parasail and *H. parasuis* type 4 bacterin administered on the same day afforded a better protection compared to 2 weeks later.

Objective

The objective of this study was to determine if ParaSail, administered per label directions and/or paired with an autogenous bacterin, protected against disease associated with an *H. parasuis* type 4 field isolate (11-1398-2; SEQ ID NO. 3).

Materials and Methods

The Parasail vaccine used was a released ParaSail serial (15B030710). The serial passed all USDA-required testing in Newport Laboratories' Quality Control facility. The potency for this serial was 8.17 logs per dose.

Autogenous vaccine: A homologous killed vaccine was prepared by growing a live culture of isolate 11-1398-2 (SEQ ID NO. 3) and inactivating the culture according to the Newport Laboratories' Standard Operating Procedure for *Haemophilus parasuis* antigen production. The potency was approximately 8.4 logs per dose.

Animals: Sixty seven pigs were received from Midwest Research Swine (Princeton site) at 17-21 days of age. All pigs were healthy and normal at time of vaccination.

Pre-challenge: A group of 10 pigs were held in a separate room and challenged 1 week prior to the study challenge. This group aided in determining an appropriate challenge titer. Five pigs received 1 mL IP and 1 mL IV of a 2.45 log culture and 5 pigs received 1 mL IP and 1 mL IV of a 3.4 log culture. Animals were observed for 5 days for clinical signs of disease and death. The results are summarized in Table 1.

TABLE 1

| Titer | Clinical Signs | Death |
|---|---|---|
| 2.45 logs | 5/5 (100%) | 4/5 (80%) |
| 3.4 logs | 5/5 (100%) | 5/5 (100%) |

Based on the results of the pre-challenge, a challenge titer of approximately 2.45 logs was selected.

Challenge: The challenge strain was a field isolate received via Prestage Farms. The strain was isolated from porcine lung tissue at MVP Laboratories and determined to be *H. parasuis* type 4. All pigs received 1 mL IV and 1 mL IP of a 2.78 log culture on the day of challenge. Table 2 summarized the schedule of events.

TABLE 2

| Day | Action |
|---|---|
| 0 | Vaccinate, bleed |
| 12 | Booster Group B pigs only, bleed |
| 26 | Pre-challenge |
| 40 | Challenge, bleed all |
| 41-44 | Observations of clinical signs |
| 44 | Necropsy, score lesions |

Treatment Groups:

A. ParaSail+Autogenous Type 4: administered simultaneously, 1 mL on either side of neck (n=15).

B. ParaSail+Autogenous Type 4: ParaSail given on day 0, autogenous given on day 12 (n=15).

C. ParaSail only: adjuvanted with Quil and Trigen (1 dose) (n=14).

D. Controls (n=13).

Observations:

Pigs were observed daily following challenge for clinical signs of disease associated with *H. parasuis* including lameness, labored breathing, vomiting, and sudden death. All observations were conducted and recorded by study personnel blinded to treatment group allocation. Any pig unable to rise was euthanized for humane reasons.

Necropsies:

Any pig that was found dead or was euthanized during the study observation period was assumed to have internal lesions including peritonitis, pleuritis, and/or pericarditis. At 5 days post-challenge all surviving pigs were euthanized and necropsied. The presence of gross lesions including peritonitis, pleuritis, pericarditis, and swollen joints were recorded.

Analysis:

Statistical analysis was performed by Tammy Kolander using SAS software.

A t-test and a Tukey HSD all-pairwise compared clinical signs, death, and the presence of lesions between the vaccinate groups and the controls. Table 3 summarizes the raw data collected for clinical signs, death, and gross lesions.

TABLE 3

| Group | Treatment | % with clinical signs (including death) | % died during the study | % with lesions at necropsy or died during study | % with lesions at necropsy (surviving pigs only) |
|---|---|---|---|---|---|
| A | ParaSail + Autogenous (simultaneous) | 0% (0/15) | 0% (0/15) | 7% (1/15) | (1/15) 7% |
| B | ParaSail + Autogenous (2 weeks between) | 20% (3/15) | 7% (1/15) | 20% (3/15) | (2/13) 15% |
| C | ParaSail (Quil + Trigen) | 21% (3/14) | 14% (2/14) | 29% (4/14) | (2/12) 17% |
| D | Control | 54% (7/13) | 38% (5/13) | 69% (9/13) | (4/8) 50% |

Statistical analysis concluded the following regarding significant differences between the vaccinated pigs and controls:

Clinical signs (including death): The t-test found the Controls to be significantly different from all the other treatments, but none of the other treatments (A-D) were significantly different from one another. Tukey's all pairwise comparison found only the Controls and Group A to be significantly different from one another, and no difference between any other combinations.

Death during observations: The t-test showed a significant difference between the Controls (group D) and Group B and between the Controls (group D) and Group A. There were no significant differences between any of the other groups. Tukey's all pairwise comparison resulted in a significant difference between Group A and the Controls; there were no differences between any other groups.

Lesions at necropsy (and death during observations): The t-test showed significant differences in the Controls verses Groups A-C, with no significant differences between groups A-C. Tukey's all pairwise comparison resulted in a significant difference between the Controls and Group A and the Controls and Group B.

Three parameters of the presence of disease caused by H. parasuis were investigated: clinical signs during observations, death during observations, and the presence of lesions at necropsy. Two different statistical tests were conducted comparing each parameter between each group. The results clearly indicate the advantage of administering H. parasuis type 4 bacterin along with Parasil formulation. Adding H. parasuis type 4 bacterin significantly reduces lung lesions, clinical signs and decreases losses due to death.

Genomic DNA Sequencing

The genomic DNA from two H. parasuis ST4 field strains (12-1322; SEQ ID NO. 2 and 11-1398-2; SEQ ID NO. 3) and ParaSail vaccine (serotype 5, ST5; SEQ ID NO. 1) was isolated using bacterial genomic DNA isolation kit (Edge Biosystems) and sequenced by Illumina HiSeq paired end 50 (PESO).

Sequence Analysis

The H. parasuis ParaSail vaccine and Genbank ST5 isolate SH0165 (accession number CP001321.1) were used as reference genomes. The genome sequence of GenBank isolate was downloaded, and ABACAS (http://abacas.sourceforge.net/) was used to align SH0165 contigs and identify putative gap sizes, orientation, and order of the contigs. A custom Python script was then used to concatenate contigs, fill the gaps with N's, and transferring the annotations. Additional annotations were added to the resulting sequence to indicate gaps, and to label the original contigs. The contigs which could not be aligned against the reference were included at the end of the concatenated sequence.

Reads were filtered for quality using a custom Python script. Low quality reads were discarded (any read containing 5 or more bases with PHRED Quality <20 was considered low quality). Because of very high coverage, duplicate reads were expected and reads were only kept if at least 2 duplicates existed. A maximum of 10 duplicates were kept for each read. Following quality filtering, reads were mapped against SH0165, a concatenated set of contigs aligned and oriented using SH0165 as a reference. Reads were mapped using Bowtie2 v 2.0.6. Reads for each isolate were mapped against H. parasuis ParaSail vaccine (HSP_ref) using bowtie2 with default parameters. Filtering was then carried out to remove multiply mapped reads and MAPQ <10 using a custom script.

The Sequence Alignment/Map (SAM) output from Bowtie2 was then further analyzed using the SAMtools package in order to call variants. The resulting variant calls were then further analyzed using a custom script written in R in which variants were annotated based on their position within the genome. Variants were also filtered based on depth of coverage, and the genotype quality reported by SAMtools. SAMtools was also used to generate a consensus sequences based on the mapping results. This sequence was annotated using the reference sequence and formatted as a Genbank file for Artemis compatibility using custom scripts and BioPython.

Reads which could not be mapped to the reference by Bowtie2 (consisting of ~10% of reads) were identified and assembled using the Roche GsAssembler (Newbler) v2.6. Assemblies had a total length of 150 and 190 Kb, and consisted of 149 and 194 contigs for 51322 and 51398 respectively. The gene prediction program Prodigal v2.6 was used to predict genes in the assembled contigs, these genes were then given putative annotation using the software tool BLANNOTATOR.

Single Nucleotide Polymorphisms (SNPs) and Consensus Calls

SNPs were identified using the "SAMTools mpileup" pipeline and then filtered and annotated using a custom R script. The SNPs were identified across the 3 strains.

Gene Coverage

Mapping coverage was calculated for each position in reference using samtools. Gene annotation information was then used to calculate the percentage of bases which had coverage for each gene. Genes in which less than 80% of bases had coverage were called absent.

Gene Coverage and Overall Mapping

About 2328 genes were common to all three isolates. There were 83 genes unique to the parasail vaccine (SEQ ID NO. 1), 48 genes unique to 12-1322 (SEQ ID NO. 2) and 26 genes unique to 11-1398-2 (SEQ ID NO. 3) See FIG. 1.

The reads were filtered for quality and Illumina TruSeq adapters using an in-house script which removed reads in which 5 or more bases had a Q-value <20. We obtained 255× coverage for isolate 11-1398-2 and 300× coverage for 12-1322 respectively. Both the *H. parasuis* ST4 isolates mapped ~90% to the reference Parasail vaccine.

The *H. parasuis* ST4 strains lack enzymes such as UDP-glucose-4-epimerase, toxin-antitoxin system and a large number of hypothetical proteins.

Notable enzymes altering the outer membrane protein (OMP) and lipooliosaccharide (LOS) structure are sialyltransferase, glycosyl transferases, polysaccharide biosynthesis protein capD, spore coat polysaccharide biosynthesis protein C and polysaccharide export protein. These proteins are involved in serotype determination, immune evasion and act as virulence factors. In addition, *H. parasuis* ST4-1 (i.e., SEQ ID NO. 2) and ST4-2 (i.e., SEQ ID NO. 3) encode other virulence and virulence associated genes found in the Newport Laboratories *H. parasuis* ST5 wild type as well. The functional significance of each of these proteins and genes in comparison to *H. parasuis* ST5 and other pathogenic bacteria are discussed below.

Sialyltransferase

Sialylation of LOS has been implicated as a bacterial virulence factor by inhibiting antibody binding and enhancing bacterial serum resistance. The genes encoding the α-2, 3-sialyltransferases are involved in LOS biosynthesis in the members of pathogenic bacteria belonging to the Pasteurellaceae family, such as *Neisseria gonorrhoeae, Haemophilus ducreyi, Haemophilus influenzae* and *Histophilus somni* (Vimr and Lichtensteiger 2002; Inzana et al., 2002). Sialylated LOS aids host immune evasion by its molecular mimicry. Furthermore, pathogenic bacteria also utilize linkage-specific sialyltransferases, such as an α-2, 3 linkage to galactose, or an α-2, 6 linkage to galactose or N-acetylgalactosamine to sialylate its LOS in order to avoid host innate defense mechanisms (Inzana et al., 2002). It has been speculated that sialylated LOS induce significantly less cytokine response from macrophages by inhibiting the TLR-4 signaling pathway, which in turn induces significantly less transcription factor NF-κB than de-sialylated LOS (Vimr et al., 2000; Severi et al., 2007).

Earlier reports indicate the presence of sialyltransferase-encoding gene (lsgB) only in virulent *H. parasuis* strains, which also display a higher resistance to serum-mediated killing and phagocytosis by alveolar macrophages than strains lacking lsgB (ref). However, pigs infected with variant *H. parasuis* ST4 showed signs of acute pneumonia and septicemia indicating a "cytokine storm" as a result of infection. Furthermore, pure *H. parasuis* ST4 cultures were obtained from tissue samples. When mice were injected with a de-sialylated *P. multocida* mutant all the mice died within 48 hours due to septicemia, indicating an exuberant immune response. On the other hand, mice injected with sialylated (wild type) *P. multocida* did not die, but had injection-site swelling only (Newport Laboratories internal report).

*H. parasuis* ST4 and ST5 lack de novo sialic acid biosynthesis, but the genome encodes two tripartite ATP-independent periplasmic transporters, Neu5Ac TARP (HPM_1229, HPM_0026), a TRAP permease (HPM_0027) and CMP-Neu5 Ac synthetase gene (HPM_0608) and acylneuraminate cytidylyltransferase (HPM_1673), which indicates a sialic acid scavenge mechanism similar to *H. influenza* and synthesis of CMP-Neu5Ac.

Since the variant *H. parasuis* ST4 lack α-2, 3-sialyltransferases, we hypothesized that the amount of sialic acid coupled to LOS should be less than that of ST5. The amount of sialic acid coupled to LOS was determined after treating the cells with neuraminidase. The variant *H. parasuis* ST4 strains had significantly less sialic acid residues linked to LOS when compared to ST5 wild type (data not shown). These results contradict the current dogma that sialic acid is necessary for *H. parasuis* virulence. When variant ST4-1 (i.e., SEQ ID NO. 2) was used in challenge studies (15, 3 week old piglets) 54% showed clinical signs and died when compared to control which had 0% mortality, clearly indicating that LOS sialylation is not necessary for virulence. The variant *H. parasuis* ST4 strains possess other virulence factors that help subvert the host immune response and aid in pathogenesis. These virulence and virulence associated factors are discussed below.

Glycosyl Transferases

The variant *H. parasuis* ST4 strains lack four glycosyl transferases (HPM_1373, HPM_1372 and HPM_1370 and HPM_1371). Glycosyl transferases catalyze the reaction involving the addition of carbohydrate side group to a protein or lipid molecule. Addition of carbohydrate residues to proteins significantly alters its biophysical and structural properties like solubility index, resistance to proteases, stability, interaction with other proteins and most importantly the immunogenicity of pathogenic bacteria (Lairson et al., 2008). The two important and common types of protein glycosylation are N-linked and O-linked. N-linked glycosylation is a co-translational process involving the transfer of a precursor oligosaccharide to asparagine residues in a sequon Asn-X-Ser/Thr (N-X-S/T), where X is any amino acid other than Proline (Yan and Lennarz, 2005). In contrast, O-linked glycosylation involves the post-translational transfer of an oligosaccharide to a serine or threonine residue (Van den Steen et al., 1998). Many of the surface and secreted proteins are modified by glycosylation, which in turn affects how bacteria interact with their environment and host immune system (Szymanski and Wren, 2005; Schmidt et al., 2003). The lack of glycosyl transferases in variant *H. parasuis* ST4 strains suggests alternate pathways of glycosylation since different groups of glycosyl transferases have overlapping functions. However, many enzymes involved in cell wall biosynthesis like N-acetylmuramyl-tripeptide synthetase protein (HPM_1513), MurNAc-pentapeptide synthetase (HPM_1514), phospho-N-acetylmuramoyl-pentapeptide-transferase (HPM_1515), UDP-N-acetylmuramoyl-L-alanyl-D-glutamate synthetase (HPM_1945), D-alanine-D-alanine ligase (HPM_2304), UDP-3-O-acyl-N-acetylglucosamine deacetylase (HPM_2413) and exopolysaccharide biosynthesis protein (HPM_0770) present are identical across all three isolates (data not shown). Modified LOS and OMP glycosylation pattern of variant *H. parasuis* ST4 strains probably help avoid phagocytosis.

Polysaccharide Export Protein and Polysaccharide Biosynthesis Protein CapD

Polysaccharide export protein and polysaccharide biosynthesis protein are located as contiguous ORFs in *H. parasuis* ST4 and ST5 strains. Bacteria export extracellular polysaccharides (EPS) and capsular polysaccharides (CPS) through a complex transport system (Cuthbertson et al, 2009). These biopolymers serve various biological functions, such as providing reserve material or as part of a protective structure and can provide a substantial advantage for pathogenic bacteria under certain environmental conditions. In pathogenic bacteria, production and export of EPS and CPS poses a major challenge because these high-molecular-weight hydrophilic polymers must be assembled and exported across the envelope, without compromising the essential functional properties of the envelope (Cuthbertson et al, 2009). Two major pathways with different polymer biosynthesis strategies are employed by bacteria in the assembly of most EPS/CPS: the Wzy-dependent and ATP-binding cassette (ABC) transporter-dependent pathways (Lame et al., 2011). They converge in an outer membrane export step mediated by a member of the outer membrane auxiliary (OMA) protein family. OMA proteins form outer membrane efflux channels for the biopolymers (ref). The polysaccharide copolymerase (PCP) family of enzymes interact with OMA proteins to form a trans-envelope scaffold for polymer export (Lame et al., 2011). The variant *H. parasuis* ST4 strains have numerous ABC transporter systems similar to virulent *H. parasuis* ST5 but lack polysaccharide export protein (HPM_0299) wza. This demonstrates a functional overlap between ABC transporters in exporting complex carbohydrates and biopolymers.

The capD gene (HPM_0300) encodes a polysaccharide biosynthesis protein. This protein has been implicated in *H. parasuis* virulence, however, the characteristics of this gene associating with the pathogenicity of *H. parasuis* has not been delineated. This domain is found in diverse bacterial polysaccharide biosynthesis proteins including the WalL protein, mannosyl-transferase and epimerases (Whitfield, 2006). The CapD protein is required for biosynthesis of type 1 capsular polysaccharide in *Staphylococcus* spp. (Lin et al., 1994). In *H. parsuis* capD protein is implicated in serum-resistance. However, variant *H. parasuis* ST4-1 (i.e., SEQ ID NO. 2) and ST4-2 (i.e., SEQ ID NO. 3) strains lack this domain but are highly virulent and were recovered as pure culture from dead pigs, proving serum-resistance without capD protein. Earlier reports indicate that the deletion of capD gene significantly attenuates SH0165 pathogenicity, while the complementation of this gene largely restored the pathogenicity in piglets (Wang et al., 2013). Furthermore, the capD deleted SH0165 strains were not recovered from piglets after challenge, while both SH0165 wild type and complemented-capD strains were recovered from most systemic sites (Wang et al., 2013). In contrast to SH1065 virulent strain, the variant *H. parasuis* ST4 isolates caused a rapid onset of clinical signs and two out of the four pigs died during our study. When the pigs were necropsied we found lesions typical to *H. parasuis* infection and isolated virulent *H. parasuis* ST4, the original challenge strain.

PCR Analysis of Virulence Genes

The variant *H. parasuis* ST4-1 (i.e., SEQ ID NO. 2) and ST4-2 (i.e., SEQ ID NO. 3) strains lack ORFs HPM_1370, HPM_1371, HPM_1372, HPM_1373, HPM_0299 and HPM_0300, reiterating our in silico based analysis. On the other hand *H. parasuis* variant ST4 strains possess all three virulence associated trimeric autotransporters (vtaA) domains similar to virulent *H. parasuis* ST5. Comparative genomic analysis have indicated that group 3 vtaA is highly conserved among both invasive and non-invasive strains, while groups 1 and 2 vtaA were detected only in virulent strains (Pina et al., 2009). However, we detected all three domains in highly virulent, ST4-1 (i.e., SEQ ID NO. 2), ST4-2 (i.e., SEQ ID NO. 3), and ST5 well as in an avirulent ST5 strain (Newport Laboratories internal report). We speculate that characterization of non-virulent and virulent *H. parasuis* strains based on vtaA domains may not be a reliable approach given the complex gene regulation mechanism involved in determining *H. parasuis* virulence.

Other Virulence and Virulence Associated Genes

Other than the known virulence genes, *H. parasuis* ST4 and ST5 genomes encode a large number of other virulence and virulence associated genes. These include regulation of uptake of metal ions, MerR family transcriptional regulators, macrophage infectivity potentiator-related protein, hemolysin, opacity associated protein, toxin antitoxin system, virulence associated protein D, colicins and cytolethal distending toxin.

Regulation of Uptake of Metal Ions

Like many pathogenic bacteria, variant *H. parasuis* ST4-1 (i.e., SEQ ID NO. 2), ST4-2 (i.e., SEQ ID NO. 3) strains and ST5 have extensive regulatory and protein-coding machinery exclusively devoted to maintain the homeostasis of biologically required metal ions. Most of these metal ions must be acquired from the environment. Among the metal ions, iron is the chief regulator of many virulence genes and variant *H. parasuis* ST4-1 (i.e., SEQ ID NO. 2), ST4-2 (i.e., SEQ ID NO. 3) and ST5 has an extensive protein network to regulate iron. Iron is generally a growth limiting factor for pathogenic bacteria due to the low solubility of Fe(III) in water at neutral pH, but is required for a number of essential metabolic enzymes, including the cytochromes, ribonucleotide reductase, Fe—S cluster biogenesis and activation/regulation of virulence genes (Laham and Ehrlich 2004). Most of the mammalian hosts lack free iron for uptake, since most of it is stored in intracellular or extracellular tightly bound forms like transferrin, lactoferrin, haemopexin and haptoglobin (Litwin and Calderwood 1993). Many outer membrane (OM) receptor proteins like ferroxamine (HPM_2297) first bind to lactoferrin or ferritin and mediate the transport. These receptors are usually 22-stranded β-barrel proteins that contain extracellular loops that bind substrates, and an N-terminal region or plug, that folds into the barrel near the periplasmic surface (Ferguson et al., 2002). Since there are no ionic gradient to drive this transport, transport across the OM is coupled to the proton motive force of the cytoplasmic membrane via a periplasm-spanning complex composed of TonB (HPM_0089 and HPM_0090), ExbB (HPM_0091), and ExbD (HPM_0092) (Braun et al., 1996). Once in the periplasm, the uptake of Fe (III) or Fe (III)-chelates occurs through the transmembrane channel of ATP-binding cassette (ABC) transporters (Davidson et al., 2008) found in the plasma membrane. This process is mediated by ATP hydrolysis. *H. parasuis* ST4 and ST5 also possess three heme binding proteins (HPM_0689, HPM_2386 and HPM_0785) which bind to heme and hemin and are involved in heme acquisition. Variant *H. parasuis* ST4 also encodes iron-binding protein IscA (HPM_1829), which transfers intracellular free iron to, for example, apo-ferredoxin, iron utilization protein hugX (HPM_0784), ferric iron reductase (HPM_1543, involved in ferric hydroximate transport), very high affinity iron scavenging proteins hemopexin B and A (HPM_1235 and HPM_1236), two periplasmic iron uptake and binding proteins (HPM_1161 and HPM_1150), ferric transporter ATP-binding subunit (HPM_1466), and high affinity heme/hemopexin utilization protein C/outer membrane receptor protein (HPM_1031; transports Fe ions) and ferric uptake regulation protein (HPM_1051). The heme exporter protein B (HPM_2191), which exports heme to the periplasm for the biogenesis of c-type cytochromes, is adjacent to cytochrome c biogenesis ATP-binding export protein CcmA (HPM_2192). *H. parasuis* ST4 and ST5 encode two outer membrane TonB dependent receptors or iron regulated outer membrane proteins, IROMP (HPM_0168 and HPM_0415). *H. parasuis* ST5 and ST4 also encode three small multifunctional proteins, frataxin (HPM_1028), ferredoxins (HPM_0902) and Ferritin/DNA-binding stress protein (HPM_2074). Frataxin acts as an iron chaperone during cellular heme and iron-sulfur (Fe—S) cluster production, scavenges iron and stores iron during iron overload, repairs oxidatively damaged aconitase Fe—S clusters, reduces oxidative stress by moderating the concentration of reactive oxygen species (ROS) and is involved in energy conversion and oxidative phosphorylation. Ferredoxins are proteins containing iron and sulfur atoms organized as iron-sulfur clusters (4Fe-4S), which are involved in electron transfer during biological redox reactions (Carvajal et al., 1996). The function of ferredoxins overlaps with the formate dehydrogenase iron-sulfur subunit. It contains hydrogenase component 1 (HPM_1699) which is involved in the use of formate as a major electron donor during aerobic respiration. Ferritin is another cytoplasmic protein that binds and sequesters iron and releases in a controlled fashion. In addition, ferritin binds to DNA and delivers iron into the nucleus for iron-dependent enzyme or transcription factors (Prince and Grossman, 1993; Demple et al., 1999; Khoroshilova et al., 1997). Thus, *H. parasuis* ST4-1 (i.e., SEQ ID NO. 2), ST4-2 (i.e., SEQ ID NO. 3) and ST5 genomes encode a large number of proteins with overlapping functions involved in maintaining iron homeostasis, indicating the critical role of iron in *H. parasuis* pathogenesis. These proteins can also be targeted to develop universal vaccines or for strain identification.

In addition to iron, *H. parasuis* also requires metal ions like molybdenum, zinc, copper, nickel, magnesium for the activation of many metalloproteases, metabolic enzymes and DNAse. *H. parasuis* ST4-1 (i.e., SEQ ID NO. 2), ST4-2 (i.e., SEQ ID NO. 3) and ST5 has an extensive network of proteins to acquire these metals which include molybdenum cofactor biosynthesis (HPM_0200), molybdoprotein biosynthesis protein, molybdoprotein biosynthesis MoeB and two MoeA (HPM_0201, HPM_1239 and HPM_1012, respectively), moylbdate ATP transporter (HPM_1718), molybdate ABC transporter (HPM_1719), molybdenum transport protein (HPM_0692), molybdate-binding periplasmic protein (HPM_0693), molybdenum cofactor biosynthesis protein C' (HPM_0289), molybdopterin converting factor (HPM_0290), zinc ABC transporter (HPM_0361, HPM_1198), high-affinity zinc transporter periplasmic component (HPM_0485), zinc/copper dismutase (HPM_0873), copper homeostasis (HPM_1035), nickel transport permease (HPM_2246), nickel-binding periplasmic precursor protein, nikA (HPM_0691), ABC-type nickel/cobalt efflux system, permease component (HPM_2454), $Mg^{2+}/Co^{2+}$ transporter (HPM_2352), magnesium dismutase (HPM_1717), and magnesium transport corA protein (HPM_0841).

MerR Family Transcriptional Regulators

The regulation of metal ion homeostasis is exclusively controlled by MerR family of transcriptional regulators. MerR family of regulators has been found in a wide range of bacteria, but none have been identified in archaea or eukaryotes. MerR transcriptional regulators function mainly as transcriptional activators of the expression of genes required for metal efflux or detoxification, defense against oxidative, biotic or abiotic stress and provide drug resistance (Lund et al., 1986). *H. parasuis* ST4 and ST5 MerR regulator (HPM_1347) is a 15.7 KDa protein and belongs to the helix-turn-helix (HTH) MerR-SF superfamily. *H. parasuis* MerR is similar to other bacterial MerR regulatory proteins and follows a canonical N-terminal HTH-DNA binding domain of about 40 amino acids. It further contains a C-terminal metal-coordinating domain of between 80-130 amino acids that is specific to the effector (metal ion) recognized (O'Halloran et al., 1989; Ma et al., 2009). The MerR families of metal-binding, metal-responsive proteins are unique in that they activate transcription from unusual promoters with a high spacing of 19 base pairs between the −35 and −10 sequences (O'Halloran et al., 1989). These cytoplasmic transcription factors coordinate (bind) metals through cysteine or histidine residues (Ma et al., 2009). Although different bacteria have a common design (i.e., conserved primary structure), they can effectively discriminate metals in vivo (Brown et al., 2003). Based on NCBI analysis (E-value: 7.89e-39) *H. parasuis* Mer R regulator appears to be heavy metal (copper, cadmium, lead, zinc) resistance transcription regulator.

Taken together, the presence of extensive metal acquisition genes along with a specific transcription regulator shows a very complex gene regulation mechanism involved in the expression of *H. parasuis* virulence genes.

Macrophage Infectivity Potentiator-Related Protein

Macrophage infectivity potentiator (MIP)-related protein has been identified in many pathogenic bacteria, such as *Neisseria*, *Actinobacillus*, *Legionella* and *Chlamydia*. It has also been identified in intracellular pathogens *Coxiella burnetii*, *Burkholderia pseudomallei* and a protozoan parasite, *Trypanosoma cruzi* (Lundemose et al., 1993; Masuzawa et al., 1997; Norville et al., 2011; Pereira et al., 2002). Variant *H. parasuis* ST4 and ST5 genomes encode a putative macrophage infectivity potentiator-related protein (HPM_0216), which is a 20 Kda outer membrane protein. Analysis shows that *H. parasuis* ST4 and ST5 MIP belongs to carboxymuconolactone decarboxylase superfamily (CMD superfamily; COG2128) indicating a multidomain architecture. *H. parasuis* ST5 and ST4 MIP contains an overlapping alkylhydroperoxidase AhpD family core domain, alkylhydroperoxidase domain protein (Avi_7169 family) and a gamma-carboxymuconolactone decarboxylase. Like the rest of the prokaryotic MIP-like proteins, the predicted N-terminal structure of *H. parasuis* ST4 and ST5 MIP contains three large alpha-helices followed by a short beta-sheet or turn.

*B. pseudomallei* MIP-like protein is sensitive to immunosuppressants like FK506 and rapamycin, which abolish its peptidylprolyl isomerase activity. *B. pseudomallei* mutants lacking MIP exhibit reduced ability to survive within cells and are significantly attenuated in vivo (Norville et al., 2011). In addition, MIP has been implicated to play a role in chlamydial entry into McCoy cells (Lundemorse et al., 1993). A similar function for *H. parasuis* MIP cannot be ruled out and may aid in intracellular invasion and survival of the bacteria. MIP-like proteins could potentially serve as a target for a universal vaccine.

Hemolysin

Hemolysins are toxic to erythrocytes, but some bacterial species produce hemolysins which lyse leukocytes as well (Cavalieri et al., 1984; Forestier and Welch 1991; Gadebeerg et al., 1983; Keane et al., 1987; Wiles et al., 2008). The variant *H. parasuis* ST4-1 (i.e., SEQ ID NO. 2), ST4-2 (i.e., SEQ ID NO. 3) and ST5 have two hemolysin activation/secretion proteins (HPM_2302 and HPM_1788) and two hemolysin structural proteins (HPM_1789 and HPM_2290). The ORFs HPM_1788 and HPM_1789 are adjacent to each other, similar to *H. ducreyi* (hhdB and hhdA), *Serratia marcescens* (shlB and shlA), *Proteus mirabilis* (hpmA and hpmB) and *Edwardsiella tarda*. However, ORFs HPM_2302 and HPM_2290 are nonadjacent. In addition, *H. parasuis* ST4 and ST5 genomes also encode AphA-like protein/membrane protein affecting hemolysin expression (HPM_2138), a 21 kDa hemolysin precursor protein (HPM_0599) and another possible hemolysin structural protein (HPM_0082). Earlier studies have shown that the *S. marcescens* ShlB protein is an outer membrane protein, which is required for secretion and activation of the hemolysin structural protein, ShlA (Konninger et al., 1999). Once secreted, ShlA interacts with target cell membranes, oligomerizes, and forms pores on the cell membrane resulting in target cell lysis similar to other members of the "RTX" toxin family (Schönherr et al., 1994).

*H. ducreyi* strains expressing cloned hemolysin genes showed a ten-fold increase in invasion of human epithelial cells when compared to the control strain (Wood et al., 1999). The target cell range of *H. ducreyi* hemolysin includes T-cells, macrophages, human foreskin fibroblasts, human foreskin epithelial cells and B cells. PMNs were relatively insensitive to lysis by hemolysin (Wood et al., 1999). Secretion and activation of hemolysin by pathogenic bacteria is tightly regulated by iron.

Opacity Associated Protein

The opacity-associated proteins (OapA and OapB) have been implicated in phase variation, adhesion to epithelial cells during initial colonization and cell invasion in *H. influenza* and *Neisseria gonorrae* (Weiser et al., 1995; Blake and Gotschich 1984). *H. parsuis* ST5 and variant ST4 isolates encode two OapA and OapB proteins (HPM_0924 and HPM_0925) which help in initial colonization and adhesion along with fimbriae/adhesins and pili complex loci (HPM_0366, (HPM_0367, HPM_0368, HPM_0371, HPM_1452, HPM_1455 and HPM_1637).

Toxin-Antitoxin System

*H. parsuis* ST4 and ST5 genomes encode numerous toxin-antitoxin systems (TAS) which are abundant, diverse, horizontally mobile genetic elements (Arcus et al., 2004; Buts et al., 2005; Zielenkiewicz and Ceglowski 2001). TAS are mostly limited to bacterial and archaeal genomes and are involved in a variety of functions, including plasmid stabilization, transcription regulation, enhancing resistance mechanisms and RNA-interference (Pandey et al., 2005; Buts et al., 2005; Zielenkiewicz and Ceglowski 2001). *H. parsuis* ST4 and ST5 TAS modules include the host-death prevention family protein/antitoxin of toxin-antitoxin stability system (HPM_1007), antitoxin/toxin system zeta toxin, signal recognition particle GTPase protein (HPM_1145), fic family toxin-antitoxin (HPM_1182), addiction module antitoxin/putative RelE toxin-like protein, plasmid stabilization system (HPM_1184), toxin component RelE family (HPM_0312), transcriptional regulator/antitoxin, MazE protein (HPM_1226), antitoxin ChpS/transcriptional regulator/antitoxin, MazE/putative plasmid stable inheritance protein (HPM_1862), growth inhibitor, PemK-like autoregulated/transcriptional modulator of MazE/toxin, MazF, plasmid stable inheritance protein K protein (HPM_1863), plasmid stability protein StbD (HPM_2272), HicA and B (HPM_2185, HPM_0011 and HPM_0012). The number of modules in a TAS may range from one to eight (Mittenhuber 1999; Gerdes 2000). Most of the regulated TSS are two-component systems and function similar to HicA and HicB. The ORFs HicA and B (HPM_0011 and HPM_0012) are contiguous and attached to competence protein comM (HPM_0013), whereas another HicA (HPM_2185) is associated with an endonuclease (HPM_2184). The HicB protein has a partially degraded RNAse H fold, whereas HicA contains a double-stranded RNA-binding domain (Markarova et al., 2006). The stable combination of these two domains clearly suggests transcription regulation mediated through RNA, most probably by RNA binding-degradation (i.e., RNA interference) mechanism. In most HicB proteins, the RNAse H-like domain is fused to a DNA-binding domain, of the ribbon-helix-helix or to the helix-turn-helix motif. The TAS proteins containing these DNA-binding domains function as antitoxins (Markarova et al., 2006). *H. parasuis* ST4 and ST5 isolates have numerous TAS genes located within their pathogenicity islands (PAIS) that are amenable for horizontal transfer and function as accessory to chief virulence genes.

Virulence Associated Protein D

*H. parasuis* ST4 and ST5 genomes encode virulence associated protein D (VapD; HPM_1572) which shows 100% identity to VapD of *H. parasuis* SH0165 (YP_002476324), *H. parasuis* ZJ0906 (YP_008124455) and *H. parasuis* SW114 (EQA00157.1), but are only 90% identical to *Actinobacillus minor* (WP_005826028), 64% identical to *Neisseria lactamica* (WP_003711106.1), 63% identical to *N. meningitides* (WP_002238271.1), and 62% identical to a CRISPR associated Cas2 family protein of *N. meningitides* (WP_002251489). *Rhodococcus equi* isolated from foals contains a highly characterized vapD gene on an 80-90 kb virulence plasmid (Giguere et al., 1999). The *R. equi* virulence plasmid contains a 27.5 kb pathogenicity island encoding a family of seven Vap proteins including VapA-G (Jain et al., 2003). *R. equi* mutants lacking 7.9 kb DNA region spanning five vap genes (vapA, -C, -D, -E and -F) are avirulent and rapidly cleared by the mouse immune system compared to wild type (Jain et al., 2003). Furthermore, isogenic plasmid-cured mutants of *R. equi* strains lose their ability to survive in alveolar macrophages and fail to induce pneumonia in foals (Hondalus and Mosser, 1994; Hondalus 1997). The vap genes are also induced by $H_2O_2$ (Benoit et al., 2002). The VapD protein along with macrophage infectivity potentiator may be involved in initiating and maintaining *H. parasuis* intracellular infection, especially within macrophages. Therefore these antigens could be incorporated in a novel vaccine development strategy.

Colicin

Colicins are heat-labile proteins first identified in certain strains of *Escherichia coli* that harbor one colicinogenic plasmid (Feldgarden and Riley, 1999). Colicins have since been identified in many bacterial strains antagonistic to another closely related strain. Colicinogenic strains of pathogenic bacteria are widely distributed in nature and are particularly abundant in the guts of animals (Cascales et al., 2007). *H. parasuis* ST4 and ST5 colicins are not synthesized under normal conditions since the colicin operon is repressed by LexA protein (HPM_1027). *H. parasuis* ST4 and ST5 encode colicin V (HPM_1084) and a colicin transport protein TolQ (HPM_1307) conferring to these strains a competitive advantage in occupying the nasal cavities and the upper respiratory tract of pigs.

Cytolethal Distending Toxins (CTDs)

Cytolethal distending toxins have been identified in various gram negative bacteria including *Campylobacter* spp. (ref), *E. coli* (ref), *Haemophilus ducreyi* (ref), *Actinobacillus actinomycetemcomitans* (ref), *Shigella dysenteriae* (ref), and *Helicobacter* spp. (ref). CDTs are heterotrimeric toxins (Johnson et al., 1988; Picket t et al., 1994; Cope et al., 1997; Mayer et al., 1999; Okuda et al., 1995; Young et al., 2000). Once CDTs enter the target cells, CTDs randomly nick cellular DNA, leading to apoptosis (Jinadasa et al., 2011). These toxins also trigger G2/M cell cycle arrest in specific mammalian cell lines, leading to enlarged or distended cells and cause necrosis (Elwell and Dreyfus 2000). The toxin is internalized via the Golgi complex and transported to the endoplasmic reticulum in a retrograde fashion similar to Cholera Toxin A1 (Teter et al., 2002). CDT production is dependent on the expression of three contiguous genes (cdtA, cdtB, and cdtC) in the operon (Matsuda et al., 2008; Dreyfus 2003). However, *H. parasuis* ST4 and ST5 genomes contain one only gene encoding CTD internalizing protein (cdtA; HPA_2217), but lack the active toxin cdtB and an internalizing protein, cdtC. The possible reasons for missing cdtB and cdtC genes include a gap in the map-based assembly or they may lack a functional CTD operon. In human infections CDT-negative *Campylobacter* strains have been isolated from patients suffering with enteric disease, indicating that CDT expression may be inconsequential for virulence (Abuoun et al., 2005), similar to virulent *H. parasuis* ST4 strains.

Unmapped Genes

Analysis of the unmapped regions yielded 263 genes for ST4-1 (i.e., SEQ ID NO. 2) and 323 genes for ST4-2 (i.e., SEQ ID NO. 3) (data not shown). ORFs less than 300 base pairs are usually repeats and often do not encode any functional proteins. Therefore, a cut off value of 300 base pairs was set and ORFs ≥300 base pairs were mapped and annotated. This yielded 190 ORFs for ST4-1 (i.e., SEQ ID NO. 2) and 237 ORFs for ST4-2 (i.e., SEQ ID NO. 3). The unmapped regions of ST4-1 (i.e., SEQ ID NO. 2) and ST4-2 (i.e., SEQ ID NO. 3) contain horizontal gene transfer elements, hypothetical proteins, transcription factors, phage genomes, transporters, housekeeping genes (cell wall/LPS biosynthesis) and a toxin antitoxin protein zeta toxin. The uniqueness of these genes to each strain could not be verified since this was a map-based assembly on draft genomes.

Single Nucleotide Polymorphisms (SNPs)

We identified 40,000+ synonymous and nonsynonymous SNPs across all 3 isolates (data not shown). These SNPs span known virulence genes, virulence-associated genes and house-keeping genes. This data will be used to design SNP arrays that will aid in studying variation across strains and will potentially aid in understanding gene regulation and the mode of action of various virulence factors.

Taken together, comparative genomic analysis indicates that the variant *H. parasuis* ST4-1 (i.e., SEQ ID NO. 2) and ST4-2 (i.e., SEQ ID NO. 3) strains have extensive LOS and OMP structure modifications which aid in nasal colonization, host immune evasion and possibly afford serum resistance. Furthermore, the lack of sialic acid residues on OMP and LOS causes uncontrolled release of cytokines leading to septicemia, pulmonary edema and severe pneumonia, as indicated by the lung pathology. When piglets were challenged with variant *H. parasuis* ST4, 50% of them died within 48 hours. Clearly, the variant ST4 strain is highly virulent. The variant *H. parasuis* ST4 also possesses a more diverse repertoire of virulence and virulence associated genes than previously described. The combination of capsule modification and phase variation due to LOS substitutions would help variant *H. parasuis* ST4 escape host immune system and morph into a deadly pathogen which may lead to an outbreak.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

SEQUENCE LISTING

The patent contains a lengthy “Sequence Listing” section. A copy of the “Sequence Listing” is available in electronic form from the USPTO web site (http://seqdata.uspto.gov/?pageRequest=docDetail&DocID=US09504740B2). An electronic copy of the “Sequence Listing” will also be available from the USPTO upon request and payment of the fee set forth in 37 CFR 1.19(b)(3).

What is claimed:

1. A vaccine for *Haemophilus* parasuis, serovar type 4, comprising a veterinarily acceptable carrier and an immunologically effective amount of killed bacterin or bacterial cell culture capable of triggering an immune response that protects swine against *Haemophilus* parasuis infection;

wherein the DNA sequence of the bacterin or bacterial cell culture comprises SEQ ID NO: 2; and wherein the killed bacterin or bacterial cell culture is chemically inactivated.

2. A vaccine for *Haemophilus* parasuis, serovar type 4, comprising a veterinarily acceptable carrier and an immunologically effective amount of killed bacterin or bacterial cell culture capable of triggering an immune response that protects swine against *Haemophilus* parasuis infection, wherein the DNA sequence of the bacterin or bacterial cell culture comprises SEQ ID NO: 3; and wherein the killed bacterin or bacterial cell culture is chemically inactivated.

3. The vaccine of claim 1, further comprising the vaccine against *Haemophilus* parasuis, serovar type 5 according to SEQ ID NO: 1.

4. The vaccine of claim 2, further comprising the vaccine against *Haemophilus* parasuis, serovar type 5 according to SEQ ID NO: 1.

5. A method for vaccinating swine against *Haemophilus* parasuis infection, serovar type 4, comprising the step of administering the vaccine of claim 1.

6. A method for vaccinating swine against *Haemophilus* parasuis infection, serovar type 4, comprising the step of administering the vaccine of claim 2.

7. A method for vaccinating swine against *Haemophilus* parasuis infection, serovar type 4, comprising the step of administering the vaccine of claim 3.

8. A method for vaccinating swine against *Haemophilus* parasuis infection, serovar type 4, comprising the step of administering the vaccine of claim 4.

* * * * *